United States Patent [19]

Konishi

[11] 4,031,205

[45] June 21, 1977

[54] METHOD FOR TREATING NERVOUS BLADDER

[75] Inventor: Toji Konishi, Tokyo, Japan

[73] Assignee: Eisai Co., Ltd., Tokyo, Japan

[22] Filed: Dec. 31, 1975

[21] Appl. No.: 645,912

[52] U.S. Cl. .................................................. 424/94
[51] Int. Cl.$^2$ ........................................ A61K 37/48
[58] Field of Search ..................................... 424/94

[56] References Cited

UNITED STATES PATENTS

| | | | |
|---|---|---|---|
| 3,113,073 | 12/1963 | Grim | 424/94 |
| 3,317,381 | 5/1967 | Umehara | 424/94 |
| 3,426,125 | 2/1969 | Shigeta et al. | 424/94 |
| 3,534,137 | 10/1970 | Matsumura et al. | 424/94 |
| 3,560,612 | 2/1971 | Matsumura et al. | 424/94 |
| 3,808,330 | 4/1974 | Ohtake et al. | 424/94 |

Primary Examiner—Jerome D. Goldberg

Attorney, Agent, or Firm—Wenderoth, Lind & Ponack

[57] ABSTRACT

A method for treating nervous bladder comprising administering to a human suffering from nervous bladder a therapeutically effective amount of Ubiquinone n represented by the following formula:

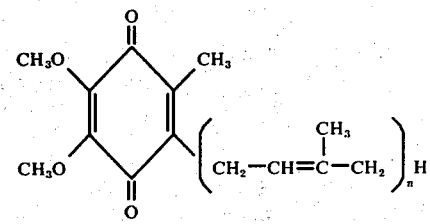

wherein $n$ represents the integer from 0 to 10, whereby nervous bladder can be treated without side-effects.

5 Claims, No Drawings

METHOD FOR TREATING NERVOUS BLADDER

This invention relates to a method for treating nervous bladder by administering to a human suffering from nervous bladder a therapeutically effective amount of Ubiquinone $n$ represented by the general formula:

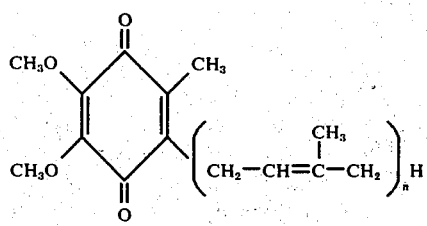

wherein $n$ represents the integer from 0 to 10.

Ubiquinone $n$ is also called "coenzyme Qn". Ubiquinone $n$ is a crystalline quinone-type compound discovered from the lipid in mitochondria of the ox heart by Crane et Wisconsin University in 1959. Though effects of Ubiquinone $n$ in vivo are not as yet sufficiently known, it has been generally thought to be a coenzyme participating in an electron transmission in mitochondria.

A nervous bladder due to the nervous disorder of bladder is sometimes caused by surgical operations of rectal cancer and by other illnesses around the bladder, and such nervous bladder is a very annoying disease accompanied by dysuria and anischuria. Recently, in particular, when rectal cancer is operated on, the efferent and afferent nerve fibers distributed in the bladder have often been impaired, thereby occurring a high frequency of dysuria. From the patho-physiological standpoint, the dysuria can be mainly thought to be the insufficiency of nervous pelvicus (parasympathetic system). Thus, the patient suffers from so-called nervous bladder, whereby ischouria paradoxa is often developed.

Because the urination is an urgent problem for the patient, it is desired that an effective method for treating nervous bladder should be established.

There are conventionally used, for the treatment of the nervous bladder, several kinds of drugs including neurotropic vitamins such as vitamins $B_1$, $B_6$, $B_{12}$, and E and parasympathetic accelerators such as Besanecol chloride, neostigmine, and dystigmine bromide. Since parasympathetic accelerators have strong side-effects, however, it is often impossible to administer high dose of such accelerators for a long duration of time continuously.

The inventor has studied various drugs to search for an effective one that can be administered continuously for the treatment of nervous bladder, and has found that Ubiquinone $n$ represented by the following formula is effective.

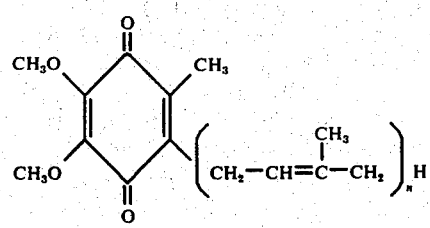

In the formula, $n$ represents the integer from 0 to 10.

The object of the present invention is therefore to provide a novel drug Ubiquinone $n$ which can be continuously administered without side-effects for the treatment of nervous bladder.

Ubiquinone $n$ of the present invention includes Ubiquinone 9 and Ubiquinone 10, both of which can be used respectively, or in combination, though Ubiquinone 10($CoQ_{10}$) is rather preferable.

Ubiquinone $n$, for example, Ubiquinone 10($CoQ_{10}$), can be mainly obtained synthetically, though it is possible to extract the Ubiquinone from animal organs. Physical and chemical properties of Ubiquinone 10($CoQ_{10}$) produced synthetically are as follows.

1. Properties

Ubiquinone 10($CoQ_{10}$) is yellow or orange crystalline powder; easily soluble in chloroform, benzene and carbon tetrachloride; soluble in acetone and ether; insoluble in ethanol; and hardly soluble in water and methanol.

2. Melting point

Approximately 48° C.

1. Acute toxicity test

In order to evaluate the acute toxicity of a single high dose administration of Ubiquinone 10($CoQ_{10}$), male and female rats of Wistar strain and male and female mice of ICR-JCL strain were used, and oral, intramuscular, subcutaneous, and intravenous administrations were studied. For the oral administration of Ubiquinone 10($CoQ_{10}$), gum Arabic suspension was used. For the intramuscular, subcutaneous, and intravenous administrations, Ubiquinone 10($CoQ_{10}$) is used as its solution in surfactant, hydrogenated castor oil ethylene oxide addition product (HCO-60).

Observation was carried out for 7 days, by using six males and six females for each dose group. In any administration group, no change was recognized in the general condition, the body weight, the food intake, and the autopsy findings. As shown in the following Table 1, there was no case of deaths in rats and mice, at the maximum dose in each administration rout.

Table 1

| Animal | Maximum dose (mg/Kg) by various routes | | | |
|---|---|---|---|---|
| | Oral | Intramuscular | Subcutaneous | Intravenous |
| Rats | 4000 | 500 | 500 | 250 |
| Mice | 4000 | 500 | 500 | 250 |

From the results described above, it can be concluded that the toxicity of Ubiquinone 10($CoQ_{10}$) is extremely low and that $LD_{50}$ of Ubiquinone 10($CoQ_{10}$) is far higher than the maximum dose mentioned above.

2. Subacute toxicity test a. Subacute toxicity test in rats

Ubiquinone 10($CoQ_{10}$) was compulsorily and orally administered every day for 5 weeks to each group consisting of 10 male rats and 10 female rats of Wistar strain. The dose was 40, 200, and 1000 mg/Kg/day, respectively. Ubiquinone 10($CoQ_{10}$) was used in the form of gum Arabic suspension, while the solution containing gum Arabic alone was used as the control group. Collection of blood and urine samples and autopsies were carried out 5 weeks after the initiation of administration.

By comparing the administration group with the control group, there was shown no difference in connection with the general condition and the body weight of the animals during the period of administration. With respect to 4 dead animals during the experiment, the autopsies revealed that they had spontaneous pneumonia and aspiration pneumonia due to the error of administration.

No significant change was recognized from the hematological test and the biochemical test of blood and urine.

In the morphological observation, there was no significant change in the weight of each organ. Further, in the macroscopical and histological observation by hematoxylin.Eosine staining and liver fat staining, abnormality was not recognized.

As described above, there was not recognized the toxicity seemingly due to the administration of Ubiquinone $10(CoQ_{10})$ in the subacute oral toxicity test carried out for 5 weeks.

b. Subacute oral toxicity test in rabbits

Ubiquinone $10(CoQ_{10})$ was compulsorily and orally administered every day for 23 days to each group consisting of six male rabbits and five female rabbits. The dose was 6, 60 and 600 mg/Kg/day, respectively. ubiquinone $10(CoQ_{10})$ was used in the form of gum Arabic suspension, whereas the solution containing gum Arabic alone was used as the control group. On the 24th day, blood samples were collected from all the animals, and three males and two females from each group were then selectively autopsied.

With reference to the general condition and the increase of body weight during the period of administration, there was shown no difference between the administration group and the control group. Abnormal findings were not obtained in the hematological test and the biochemical test of blood.

In the morphological observation, there was no effect on the weight of each organ. Further, abnormalities were not recognized in the macroscopical and histological observation by hematoxylin.Eosine staining and liver fat staining. Furthermore, in the electron-microscopic observation of liver carried out on the respective seventh, 14th, and 24th days after the administration, there were not recognized abnormal findings on the minute structure of the liver.

As mentioned above, there were not recognized the findings wherein the toxicity of Ubiquinone $10(CoQ_{10})$ will be suggested in the subacute oral toxicity test carried out for 23 days.

3. Chronic oral toxicity test

Ubiquinone $10(CoQ_{10})$ was compulsorily and orally administered to each group consisting of 10 male rats and 10 female rats of Wistar strain for consecutive 26 weeks in a ratio of 6 days a week. The dose was 6, 60 and 600 mg/Kg/day, respectively. ubiquinone $10(CoQ_{10})$ was used in the form of gum Arabic suspension, whereas the solution containing gum Arabic alone is used as the control group. Collection of blood and urine samples and autopsies were carried out 26 weeks after the administration.

With respect to the general condition of the animals during the period of administration, there was shown no difference between the administration group and the control group, and the body weight in the administration group increased as same as that of the control group.

During the experiment, 11 males and 3 females died of spontaneous pneumonia and aspiration pneumonia due to an erroneous administration.

From the standpoint of hematological findings, the leukocytal percentages showed some increase and decrease, but do not provide the mutual relation depending upon the dose; the percentages being within extent of physiological fluctuations.

No significant change were recognized in the comparison of the administration group with the control group in the biochemical tests of blood and urine.

In the morphological observation, no significant increase and decrease in the weight of organ were shown. Further, abnormalities were not recognized in the macroscopical and histological observation by hemoxylin.Eosine staining and liver fat staining, when compared the administration group with the control group.

As described above, no toxicity was observed in the chromic oral test of Ubiquinone $10(CoQ_{10})$ carried out for 26 weeks.

4. Teratogenesis test

When the does of 6, 60, and 600 mg/Kg/day of Ubiquinone $10(CoQ_{10})$ were respectively administered to rats and mice, no adverse effects were noted in mothers, fetuses, and newborns.

As the results of the acute toxicity test, the subacute toxicity test, the chronic toxicity test, and the teratogenesis test, it was found that Ubiquinone $10(CoQ_{10})$ of the present invention was a very safe drug, without side-effects.

The dose of Ubiquinone $n$ depends on types and symptoms of nervous bladder, and usually a daily dose of about 10–150 mg can be administered to the patient.

The drug of the present invention can be administered in any form of powder, tablets, granules, capsules, injections, suppository, buccal drugs, and the like.

Powder is prepared by adsorbing Ubiquinone 10 in an excipient such as magnesium carbonate, silicic acid anhydride (Siloid and Cuplex etc. in a trade name), synthetic aluminum silicate, calcium phosphate and the like, or by an organic excipient such as lactose, cornstarch, crystalline cellulose (Avicel etc, in a trade name) glucose, hydroxypropyl cellulose, and the like.

Tablets and capsules are prepared from the above-mentioned powder in accordance with any conventional method.

Injection is prepared by making the powder water-soluble by the use of nonionic surfactant in accordance with any conventional method. As nonionic surfactants, there may be mentioned hydrogenated castor oil ethylene oxide addition product (for example, Nikko, HCO in a trade name and Emalex HC in a trade name), sorbitan fatty acid ester ethylene oxide addition product (for example, Tween in a trade name), alkylphenol ethylene oxide addition product, fatty acid ethylene oxide addition product, and sorbitan fatty acid ester (for example, Span in a trade name).

When injections are given, there can be mixed propylene glycol, glucose and the like which are conventionally used. IV The results of clinical tests are shown below, in order to explain the effects of the present invention.

1. Subjects

Six patients compalining of dysuria and incontinentia urinac due to nervous bladder were made sujects. Case 1 was nocturnal enuresis of unknown cause, Cases 2-4 were impairement of root of spinal nerve (nuclear type), and Cases 5 and 6 were spinal impairements (supra nuclear type). These types were imperfect impairements, and the condition of the bladder showed a typical nervous bladder.

2. Method of administration, dose, and measurement

Hard capsules containing 5 mg of Ubiquinone 10($CoQ_{10}$) in the present invention were orally administered.

The dose of 1-3 capsules each time was orally administered 3 times a day after meals for consecutive 3-4 weeks as a rule. Depending on cases, 10 mg of Ubiquinone 10($CoQ_{10}$) was concurrently injected. The measurement of bladder functions, that is, the measurement of the pressure curve in the bladder, was carried out in accordance with any conventional method. However, the quantitative bladder crystometrographic curve (BR) was obtained by a modified method for the crystometry. More particularly, the curve was prepared by observing the condition of weak autonomic rhythmical contraction of the bladder wall, when the sensitivity and the recording rate of a crystometer were risen after the infusion of a certain amount of the solution.

3. Clinical results

As shown in Table 2, effective results and markedly effective results were found in the 5 cases among the 6 cases.

The following are the examples of effective pharmaceutical preparations for the administration of the chemical compound in the present invention.

EXAMPLE 1

| Capsule | mg in 1 capsule |
| --- | --- |
| Ubiquinone 10($CoQ_{10}$) | 5.0 mg |
| Crystalline cellulose (Avicel) | 80.0 mg |
| Cornstarch | 20.0 mg |
| Lactose | 22.0 mg |
| Polyvinyl pyrrolidone (K-30) | 3.0 mg |
| Total | 130.0 mg |

The ingredients are uniformly mixed and filled into a hard gelatin capsule in accordance with any conventional method.

EXAMPLE 2

| | |
| --- | --- |
| Ubiquinone 10($CoQ_{10}$) | 50.0 mg |
| Crystalline cellulose (Avicel) | 400.0 mg |
| Cornstarch | 550.0 mg |
| Total | 1000.0 mg |

Ubiquinone 10($CoQ_{10}$) is dissolved in acetone. After the solution is adsorbed to crystalline cellulose, the Table 2

Effectiveness of Ubiquinone 10($CoQ_{10}$) for nervous bladder

| Case | Age and Sex | Primary illness | Chief complaint | Daily dose of $CoQ_{10}$ | Before and after administration | Residual urine | Pressure curve Volume | Pressure curve Type | Urethral R.* | Basal Pressure BR | Basal Pressure SR | Effectiveness | Evaluation |
| --- | --- | --- | --- | --- | --- | --- | --- | --- | --- | --- | --- | --- | --- |
| 1 | 22 F** | — | Nocturnal enuresis | Successive 20 days with 3 capsules | Before | 35 | 295 | High pressure | 110 | + | + | Volume increased SR disappeared | Effective |
| | | | | | After | 5 | 340 | Normal pressure | 100 | Normal | Normal | | |
| 2 | 8 F | Spina bifida | Anischuria Dysuria | Successive 30 days with 3 capsules OR Successive 20 days with 4 capsules | Before | 0 | 90 | Normal reflex | 30 | ± | — | Reflex disappeared Volume increased | Unchanged |
| | | | | | After | 0 | 110 | Normal pressure | 33 | ± | — | | |
| 3 | 7 F | Spina bifida | Anischuria | Successive 30 days with 1 capsule OR Successive 30 days with 3 capsules | Before | 75 | 150 | High pressure autonomy | γ | + | ++ | Volume increased Residual urine decreased Curve improved | Effective |
| | | | | | After | 65 | 200 | '' | γ | ± | + | | |
| 4 | 60 F | Spina bifida | Anischuria Dysuria | Successive 30 days with 3 capsules | Before | 95 | 130 | Non-restraint | 45 | ± | ± | Volume increased BR appeared Anischuria improved | Markedly effective |
| | | | | | After | 70 | 345 | '' | 49 | Normal | — | | |
| 5 | 57 M*** | Paraplegia | Anischuria Dysuria | Successive 50 days with 1 capsule | Before | 20 | 240 | Reflex | 76 | ++ | ++ | Curve improved BR SR normalized | Markedly effective |
| | | | | | After | 0 | 260 | Normal pressure | 73 | Normal | Normal | | |
| 6 | 62 M | Myelitis Adhesiva | Thmyuria Dysuria | Successive 30 days with 3 capsules | Before | 25 | 150 | Reflex | γ | + | ++ | Curve improved SR improved | Slightly effective |
| | | | | | After | γ | 150 | Reflex | γ | ± | + | | |

R* Resistance; F Female; M* Male resulting adsorbed material is dried. The product is then mixed with cornstarch and made into powder in any conventional method.

EXAMPLE 3

| Tablets | |
|---|---|
| Ubiquinone 10(CoQ$_{10}$) | 5.0 mg |
| Cornstarch | 10.0 mg |
| Refined sugar | 20.0 mg |
| Carboxymethyl cellulose calcium | 10.0 mg |
| Crystalline cellulose (Avicel) | 40.0 mg |
| Polyvinyl pyrrolidone (K-30) | 5.0 mg |
| Talc | 10.0 mg |
| Total | 100.0 mg |

5.0 Mg of Ubiquinone 10(CoQ$_{10}$) are dissolved in acetone. After the solution is adsorbed to crystalline cellulose, the resulting material is dried. The product is then mixed with cornstarch, refined sugar, and carboxymethyl cellulose calcium, and made into granules in any conventional method after adding aqueous solution of PVP(K-30) as binder. After mixing with talc as lubricant, the product is made into tablets containing 100 mg for each.

EXAMPLE 4

| Solution for injection | |
|---|---|
| Ubiquinone 10(CoQ$_{10}$) | 10.0 mg |
| Hydrogenated castor oil polyoxyethylene 40 mol ether (HCO-40) | 200.0 mg |
| Tartaric acid | 10.0 mg |
| Sodium citrate | 10.0 mg |
| Distilled water sufficient to make up the total | 2.0 ml |

Ubiquinone 10(CoQ$_{10}$) is dissolved in 200 mg of HCO-40 by heating, and to the solution there are added some portion of distilled water, 10 mg of tartaric acid, and 10 mg of sodium citrate. The remaining distilled water is added to make the solution 2 ml in total. The product is filled into a lightproof container, and the space in the container is replaced by gaseous nitrogen for air-tight sealing.

EXAMPLE 5

Capsules are produced in the same way as Example 1, except for the substitution of Ubiquinone 10(CoQ$_{10}$) in Example 1 for Ubiquinone 9(CoQ$_9$).

EXAMPLE 6

Powder is produced in the same way as Example 2, except for the substitution of Ubiquinone 10(CoQ$_{10}$) in Example 2 for Ubiquinone 9(CoQ$_9$).

EXAMPLE 7

Tablets are produced in the same way as Example 3, except for the substitution of Ubiquinone 10(CoQ$_{10}$) in Example 3 for Ubiquinone 9(CoQ$_9$).

EXAMPLE 8

Injection solution is produced in the same way as Example 4, except for the substitution of Ubiquinone 10(CoQ$_{10}$) for Ubiquinone 9(CoQ$_9$).

What is claimed is:

1. A method for treating nervous bladder which comprises administering to a human suffering from nervous bladder an amount therapeutically effective for the treatment of nervous bladder of Ubiquinone $n$ represented by the formula

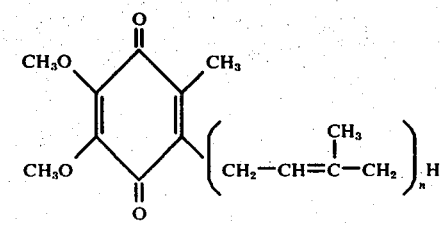

wherein $n$ represents one of the integer 9 or 10.

2. A method according to claim 1 wherein $n$ is 9.
3. A method according to claim 1 wherein $n$ is 10.
4. A method according to claim 1 wherein a daily dose of 10 – 150 mg of Ubiquinone $n$ is administered orally.
5. A method according to claim 1 wherein a daily dose of 10 – 150 mg of Ubiquinone $n$ is administered by injections.

* * * * *